United States Patent

Pavone et al.

(10) Patent No.: US 6,696,616 B2
(45) Date of Patent: Feb. 24, 2004

(54) PROCESS FOR CO-PRODUCTION OF METAXYLENE AND PARAXYLENE

(75) Inventors: Didier Pavone, Ecully (FR); Gerard Hotier, Rueil Malmaison (FR)

(73) Assignee: Institut Français du Pétrole, Rueil-Malmaison (FR)

( * ) Notice: Subject to any disclaimer, the term of this patent is extended or adjusted under 35 U.S.C. 154(b) by 0 days.

(21) Appl. No.: 09/842,262

(22) Filed: Apr. 26, 2001

(65) Prior Publication Data

US 2002/0055665 A1 May 9, 2002

(30) Foreign Application Priority Data

Apr. 27, 2000 (FR) .......................................... 00 05424

(51) Int. Cl.$^7$ .................................................. C07C 7/12
(52) U.S. Cl. ....................... 585/825; 585/820; 585/827; 585/828
(58) Field of Search .............................. 585/825, 820, 585/827, 828

(56) References Cited

U.S. PATENT DOCUMENTS 6,359,186 B1 * 3/2002 Hotier et al. ............... 585/805

FOREIGN PATENT DOCUMENTS

FR  2 782 714  3/2000

* cited by examiner

*Primary Examiner*—Walter D. Griffin
*Assistant Examiner*—Tam M. Nguyen
(74) *Attorney, Agent, or Firm*—Millen, White, Zelano & Branigan, P.C.

(57) ABSTRACT

For co-production of metaxylene and paraxylene from a hydrocarbon feedstock in a simulated moving bed in a chromatographic column (1) that contains a number of beds 1, 2, 3, 4 . . . of an adsorbent, interconnected in a loop, the column comprises an injection of the feedstock, a draw-off (14) of a first raffinate, a draw-off (17) of a second raffinate that comprises metaxylene, an injection of desorbent and a draw-off of an extract that delivers paraxylene. The injection positions and the draw-off position of the extract are offset periodically by one bed in the direction of flow of the main flux that circulates in the column. First raffinate (14) that comprises desorbent, orthoxylene, metaxylene and ethylbenzene is drawn off continuously or intermittently, and second raffinate (17) $R_2$ that comprises orthoxylene and metaxylene is drawn off intermittently. The second raffinate is distilled in such a way as to recover orthoxylene and metaxylene separately with at least 99% purity and with an improved yield. The resultant xylenes are suitable for the production of isophthalic acid and terephthalic acid

18 Claims, 3 Drawing Sheets

PROCESS FOR CO-PRODUCTION OF METAXYLENE AND PARAXYLENE

The invention relates to a process for co-production of paraxylene and metaxylene from a feedstock that contains aromatic hydrocarbons with 8 carbon atoms.

The production of paraxylene with high purity by separation by adsorption in a simulated moving bed is well known from the prior art. This market is extensively developed: its outlets are the production of terephthalic acid, phthalic anhydride and polyethylene terephthalate resins. In contrast, the metaxylene market is still restricted, whereby its outlet is isophthalic acid. It was recently perceived that the addition of small amounts of polyethylene isophthalate to polyethylene terephthalate improved the properties of the latter. It therefore becomes advantageous to co-produce paraxylene and metaxylene in the same aromatic compound production complex provided that the market requirements are satisfied: the amount of paraxylene that is produced should be much larger than that of metaxylene: typically 5 to 40 times larger, the paraxylene should be very pure, typically at least 99.6%, and the metaxylene should have reasonable purity, typically at least 99.0%.

The prior art knows metaxylene production processes, for example U.S. Pat. No. 4,326,092 where the adsorbent is a Y zeolite of an Si/Al molar ratio on the order of 4.5 to 5 exchanged with sodium and where the separation is carried out by the technique of adsorption in a simulated moving bed in liquid phase. In U.S. Pat. No. 5,382,747, the same separation is carried out on a Y zeolite that is exchanged with lithium and sodium, in a restricted range of temperature and degree of hydration by using the toluene as a desorbent. To co-produce the paraxylene in the great majority and metaxylene, the drawback of these processes is to require two separate units of very different sizes, without a possibility of finding any synergy in the co-production of the two isomers.

The prior art also describes processes of co-production of paraxylene and metaxylene; for example, U.S. Pat. No. 4,368,347 uses a vapor phase process with intermediate fraction recycling: in addition to the complication that is linked to recycling of intermediate fractions, this document does not suggest how it is possible to use in a practical way such a process that operates at a pressure of between 1 and 2 bar and at a temperature of 150 to 200° C. with a feedstock whose bubble point is 145° C. and with fixed beds that have pressure drops of at least 0.1 bar and probably more to operate economically. Patent FR 2 651 148 uses two different solvents to separate the C8-aromatic fraction into three effluents, which greatly limits its scope since the distillations that result from the simulated moving bed separation unit are multiplied. Patent WO 93/22022 describes various cases of separations of feedstocks of three components into three effluents, however the technology that is used that involves very high pressures, pressure regulation and flow rate regulation at the same time in each of the three or four zones of the process and beds that are each separated in a column is justified economically only for products of high added value.

U.S. Pat. No. 4,306,107 describes a simulated moving bed process in liquid phase where the metaxylene is sampled in the form of extract; the paraxylene, orthoxylene and a fraction of ethylbenzene are sampled as an intermediate raffinate; and finally the ethylbenzene is sampled as a raffinate. This process naturally does not allow a majority of paraxylene and an accompanying stream of metaxylene to be co-produced.

The document of the prior art that comes closest to the invention is U.S. Pat. No. 4,313,015; this document describes the separation of a simulated moving bed, in liquid phase, on zeolite X that is exchanged with barium, whereby the desorbent is diethylbenzene. The extract consists of paraxylene that is too impure (99.44%) to be marketed at current standards (current standard=99.6 mini) and with a yield of 97.5%; the intermediate raffinate consists of ethylbenzene, metaxylene and orthoxylene and a little paraxylene; finally the raffinate consists primarily of a mixture of orthoxylene and metaxylene, whereby the metaxylene can be separated by distillation. The text specifies that the intermediate raffinate is sampled approximately in the middle of the zone between the introduction point of the feedstock and the sampling point of the raffinate. The feedstock that is dealt with in the example is not completely representative of a feedstock that is found in a refinery: the latter always contain at least traces and sometimes up to 5% of paraffins and naphthenes with eight and nine carbon atoms, which distill in the same temperature interval as xylenes. This document does not specify how the paraffins and naphthenes are separated between the raffinate and the intermediate raffinate, the total number of beds and the number of beds per zone used, the order of magnitude of the flow rates in each of the zones of the process, and more particularly the one in zone 1, therefore the necessary solvent level, and the switching time of the beds (circulation speed of the solid).

One of the joint inventors of this application with two other inventors filed a patent application now publication FR 2782714 in which a process for continuous co-production of paraxylene and metaxylene from a hydrocarbon feedstock in at least one chromatographic column that contains at least twenty-five beds that are distributed in five zones is described. At least five beds should be located in zone 3B that is between the point for continuous draw-off of an intermediate raffinate that contains metaxylene, orthoxylene, ethylbenzene, solvent and paraxylene, and the point for continuous draw-off of a raffinate that contains metaxylene and orthoxylene and solvent. In addition to the large number of beds necessary for the implementation of the process (30, for example), the hydrocarbon feedstock should have an ethylbenzene content that is less than 5%, which is restricting. Furthermore, despite these constraints, although the purity of the metaxylene that is obtained after distillation under economical conditions of said raffinate is very advantageous (for example 99.6%), the yield of metaxylene relative to the metaxylene that is contained in the feedstock of the adsorption unit is about 10%, which is low.

The object of the invention is therefore the co-production of paraxylene with a purity of at least 99.6% and with a minimum yield of 98%, and metaxylene with a purity after distillation that is at least equal to 99% and with a yield that is greater than 10%, according to the definition above, and preferably greater than 15%, for example between 15 and 20%.

Another object is to produce in particular metaxylene from a feedstock that is not limited in terms of ethylbenzene.

More specifically, the invention relates to a process for co-production of metaxylene and paraxylene from a hydrocarbon feedstock that comprises them, whereby the process comprises a separation stage of said mixture in a simulated moving bed in at least one chromatographic column that contains a number of beds of an adsorbent that are interconnected in a loop, whereby said column comprises an injection of a feedstock, a draw-off of a first raffinate, a draw-off of a second raffinate that comprises metaxylene, an injection of desorbent and a draw-off of an extract that delivers paraxylene, whereby the process comprises the simultaneous periodic offsetting of injection positions and the draw-off position of the extract from a bed in the direction of flow of the main flux that circulates in the column, whereby the process is characterized in that a first raffinate that comprises desorbent, orthoxylene, metaxylene and ethylbenzene is drawn off continuously or intermittently, in that a second raffinate $R_2$ that comprises orthoxylene and metaxylene is drawn off intermittently, whereby the process is also characterized in that the second raffinate is distilled in such a way as to recover, separately, orthoxylene and metaxylene with at least 99% of purity, preferably with at least 99.5%, and with an improved yield.

The advantages of the process according to the invention relative to that of the prior art are as follows:

It is possible to work with a smaller number of beds in the chromatographic column, for example with a number of beds that is at least equal to 20.

With a number of beds that is equivalent to that of the prior art where the metaxylene is produced continuously and with an isopurity of metaxylene in the second raffinate, a better yield of metaxylene is obtained in the second raffinate relative to the initial feedstock. This yield may be multiplied by a factor of 2 relative to the one that is carried out in continuous production.

According to a characteristic of the process where the first raffinate can be drawn off continuously or intermittently, it is possible to move forward during simultaneous periodic offsetting the injection positions and the draw-off position of the extract, the position of the draw-off of the first raffinate of a bed or of two beds in the direction of the flow of the main flux.

According to a first implementation of the process where the second raffinate is drawn off intermittently, it is possible to move forward during simultaneous periodic offsetting the injection positions and the draw-off position of the extract, the draw-off position of the second raffinate of at least two beds or at most a submultiple of the total number of beds, and the second raffinate is drawn off during one period.

According to a first variant, during one period it is possible to draw off the first raffinate intermittently, the pressure of the chromatographic column is controlled at the level of the feedstock, or the desorbent or the extract, preferably at the level of the feedstock, and the first raffinate and the second raffinate are drawn off under flow monitoring.

According to this variant, the process can be implemented according to several embodiments:

A—According to a first embodiment, it is possible to draw off during a period Tn, from a given bed n, the second raffinate plus the first raffinate during next period Tn+1, from the same bed n, no raffinate is drawn off from next bed n+1, the second raffinate of next bed n+2 is drawn off during the period Tn+2, then the first raffinate during next period Tn+3 from same bed n+2, and so on.

B—According to a second embodiment, it is possible to carry out the following sequence multiple times: in a given bed n, the second raffinate is drawn off during a period Tn, in same bed n, the first raffinate is drawn off during next period Tn+1, in next bed n+1, the first raffinate is drawn off during next period Tn+2, and no raffinate is drawn off in next bed n+2.

C—According to a third embodiment, it is possible to carry out the following sequence multiple times: in a given bed n, the first raffinate is drawn off during a period Tn; in next bed n+1, the first raffinate is drawn off during a period Tn+1; in next bed n+2, the first raffinate is drawn off during a period Tn+2; no raffinate is drawn off in next bed n+3 during next period Tn+3, and a second raffinate is drawn off in next bed n+4 during same period Tn+3.

According to a second variant, to draw off the first raffinate continuously, it is possible to draw off from one bed the first raffinate for at least one period, and under pressure monitoring and during another period, a minor portion of the first raffinate is drawn off from another bed at a minimum flow rate that is compatible with pressure monitoring, and a major portion of the second raffinate is drawn off simultaneously under flow monitoring.

According to a second implementation of the process where the second raffinate is drawn off intermittently, it is possible to move forward during simultaneous periodic offsetting the injection positions and the draw-off position of the extract, the position of draw-off of the second raffinate from at least one bed or at most a submultiple of the total number of beds, and the second raffinate is drawn off during a fraction of the period.

More specifically, during a fraction of the period, it is possible to draw off from a bed a minor portion of the first raffinate under pressure monitoring and a major portion of the second raffinate under flow monitoring, then during the remaining portion of the period, only the first raffinate is drawn off from the same bed under pressure monitoring, and the sequence above is repeated in the next bed in the next period and so on.

The process according to the invention can be implemented in liquid phase at a temperature that is generally between 20° C. and 260° C., preferably between 90° C. and 210° C., and under a pressure of between atmospheric pressure and 18 bar (1 bar=0.1 MPa).

The invention will be better understood based on the following figures, among which:

A simulated moving bed device with at least three zones has already been described in the literature, for example in U.S. Pat. No. 2,985,589, and the description of its principle of operation, which is well known, will therefore not be repeated.

Figure 1:
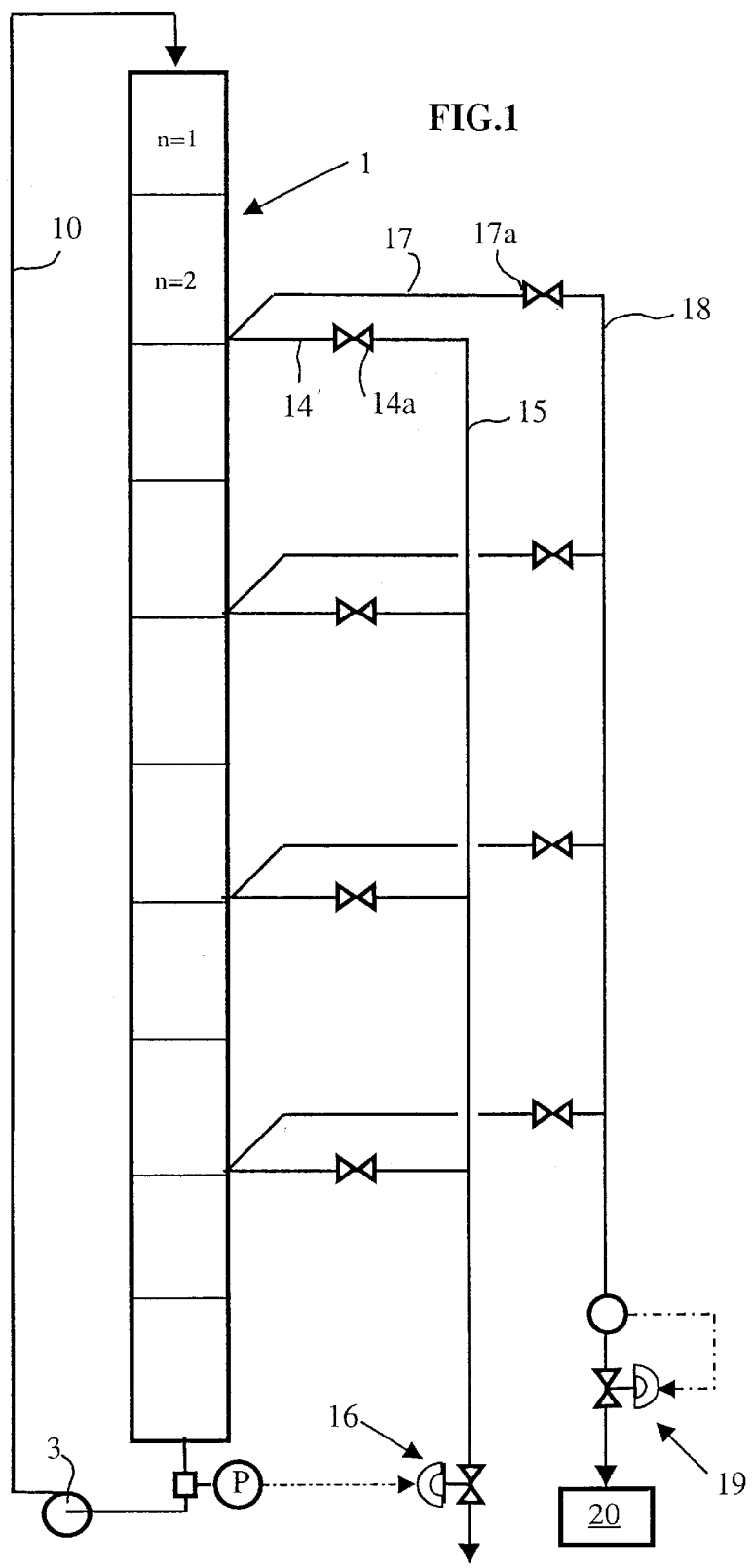
FIG. 1 illustrates the continuous production of a first raffinate according to the invention and the intermittent production of a second raffinate that contains metaxylene and orthoxylene for the duration of a period.

According to FIG. 1, the device comprises a chromatographic column 1 that is filled with a zeolitic adsorbent that comprises a number of beds n, whereby n can be equal to 24, for example. This column defines a closed loop with a line 10 that is connected to the ends of the column. The main flow circulates there, for example, from top to bottom via a recycling pump 3 in line 10. A line, not shown in the figure, injects desorbent (PDEB) into the inlet of bed 7, a line, not shown in the figure, draws off an extract that consists of desorbent and paraxylene at the outlet of bed 11 and before bed 12, and a line, not shown in the figure, injects a feedstock of xylenes (orthoxylene, metaxylene and paraxylene) and ethylbenzene into the inlet of bed 21. For reasons of simplicity, draw-off lines 14 and 17 of the first and second raffinates are shown according to the invention at the outlet of bed 2 and before bed 3. Each draw-off line 14 of the first raffinate comprises a stop valve 14a and is connected to a collecting line 15 of the first raffinate that comprises desorbent, orthoxylene, metaxylene and ethylbenzene. The pressure of the system that is measured upstream from the recycling pump is monitored by a pressure control valve 16 that is placed on line 15. Line 15 is connected to a distillation column, not shown in the figure.

Each draw-off line 17 of the second raffinate that contains desorbent and essentially orthoxylene and metaxylene also comprises a stop valve 17a and is connected to a collecting line 18 of the second raffinate that is under flow monitoring using control valve 19. Collecting line 18 is connected to a buffer tank 20 that is placed upstream from distillation columns, not shown in the figure, to eliminate the desorbent or to separate the metaxylene from the orthoxylene.

The continuous production of the first raffinate and the intermittent production of the second raffinate during an entire period can be shown in the following way:

If the flow rates of the two raffinates in all are equal to 100, it is possible, for example:

- to draw off from bed 2 a flow of first raffinate R1 that is equal to 25 via line 14 and a flow of second raffinate R2 that is equal to 75 via line 17 during a period Tn, then
- to draw off from same bed 2 a flow of first raffinate R1 that is equal to 100, whereby the flow of R2 is zero (valve 17a closed) during next period Tn+1.
- During period Tn+2, a flow of first raffinate R1 that is equal to 25 and a flow of second raffinate R2 that is equal to 75 are drawn off from bed 4.
- During period Tn+3, a flow of first raffinate R1 that is equal to 100 is drawn off from same bed 4, whereby the flow of the second raffinate is zero,
- and so on.

Quite obviously, at the end of each period, the position of the injections of desorbent and feedstock and the draw-off position of the extract that contains pure paraxylene are simultaneously offset from one bed in the direction of flow of the main fluid that travels through the chromatographic column, i.e., from top to bottom.

Figure 2:
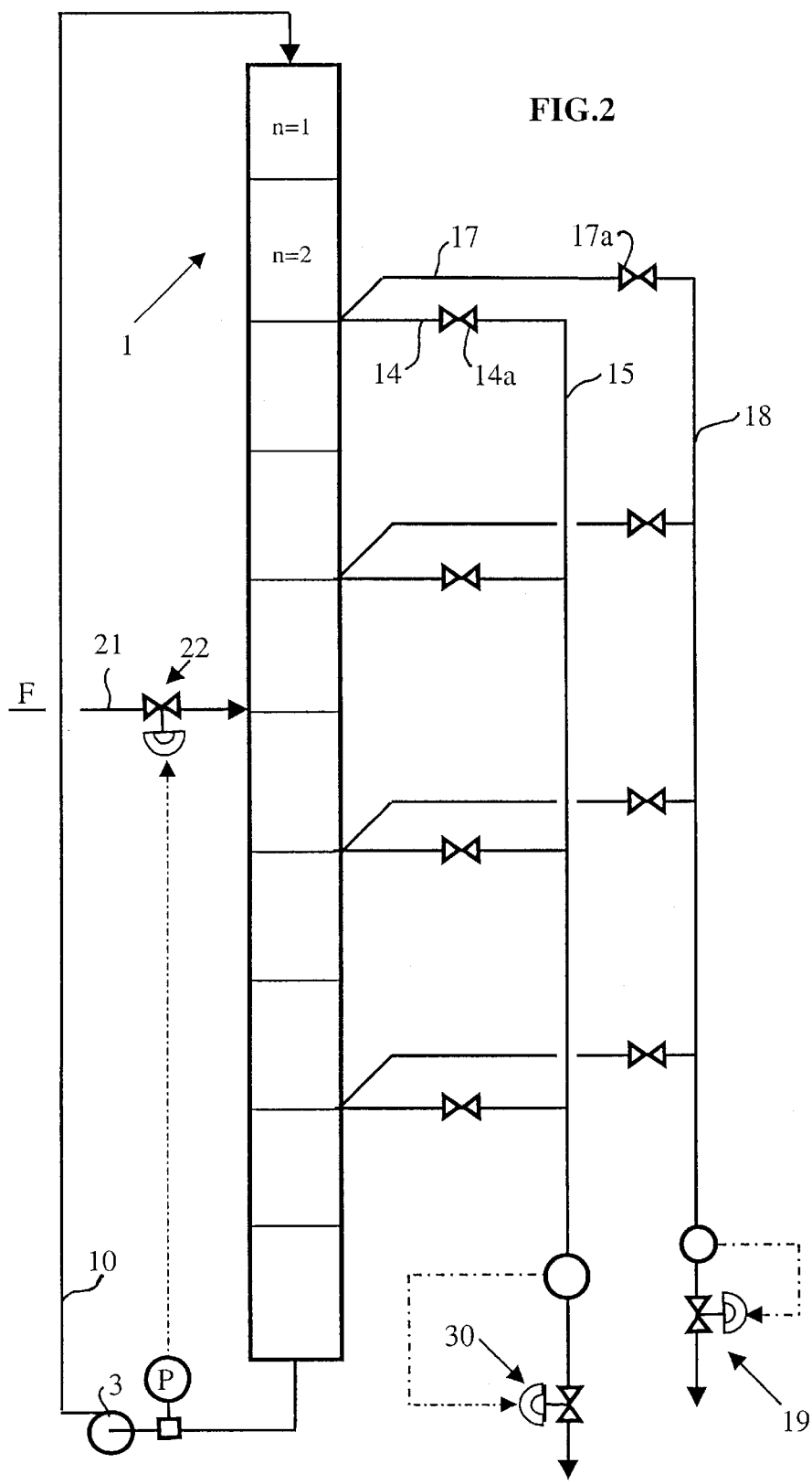
FIG. 2 illustrates the intermittent production of the first raffinate and the intermittent production of the second raffinate according to the invention for the duration of a period.

FIG. 2 describes the intermittent production of first raffinate R1 and the intermittent production of second raffinate R2 containing very pure metaxylene in particular. When they are drawn off, R1 and R2 are drawn off during one period.

The various elements of the device are numbered according to those of FIG. 1. Line 15 recovers the first raffinate, and a control valve 30 controls the flow rate. Line 18 recovers the second raffinate, and a control valve 19 controls the flow rate. Furthermore, a feedstock injection into the column via a line 21 was shown in FIG. 2, and the pressure monitoring of the system is ensured by a control valve 22 that is placed on this line 21 and connected to a measurement of pressure upstream from recycling pump 3.

It is possible to show the process operating according to Table 1, whereby the number of the bed at the injection of the feedstock, n=18, for example, indicates that the feedstock is injected into bed 18 and whereby the number of the bed at the draw-off of the extract, n=9, for example, specifies that the extract is drawn off before bed n=9, i.e., between beds 8 and 9:

TABLE 1

| Desorbent | Extract | Feedstock | R1 | R2 | Period | Raf |
|---|---|---|---|---|---|---|
| 4 | 9 | 18 | 24*0 | 1 | Tn | 1 |
| 5 | 10 | 19 | 1 | 2*0 | Tn + 1 | 1 |
| 6 | 11 | 20 | 2*0 | 3 | Tn + 2 | 3 |
| 7 | 12 | 21 | 3 | 4*0 | Tn + 3 | 3 |
| 8 | 13 | 22 | 4*0 | 5 | Tn + 4 | 5 |
| 9 | 14 | 23 | 5 | 6*0 | Tn + 5 | 5 | whereby n*0 means that the valve before bed n is closed; Raf: bed where R1 and R2 flow Thus, R1 and R2 are drawn off from both columns intermittently, whereby 50% (1 volume per 1 volume) consists of first raffinate R1 and 50% of second raffinate R2.

According to an embodiment that illustrates the case where ⅔ of the draw-off flow rate consists of the first raffinate and ⅓ consists of the second raffinate (2 volumes of R1 and one volume of R2), the device is used according to Table 2 below:

TABLE 2

| Desorbent | Extract | Feedstock | R1 | R2 | Period | Raf |
|---|---|---|---|---|---|---|
| 3 | 8 | 17 | 23*0 | 24 | Tn | 24 |
| 4 | 9 | 18 | 24 | 1*0 | Tn + 1 | 24 |
| 5 | 10 | 19 | 1 | 2*0 | Tn + 2 | 1 |
| 6 | 11 | 20 | 2*0 | 3 | Tn + 3 | 3 |
| 7 | 12 | 21 | 3 | 4*0 | Tn + 4 | 3 |
| 8 | 13 | 22 | 4 | 5*0 | Tn + 5 | 4 |
| 9 | 14 | 23 | 5*0 | 6 | Tn + 6 | 6 |
| 10 | 15 | 24 | 6 | 7*0 | Tn + 7 | 6 |

As for the embodiment that is illustrated by FIG. 2, the two raffinates are drawn off under flow monitoring while the feedstock, for example, is injected under pressure monitoring.

Figure 3:
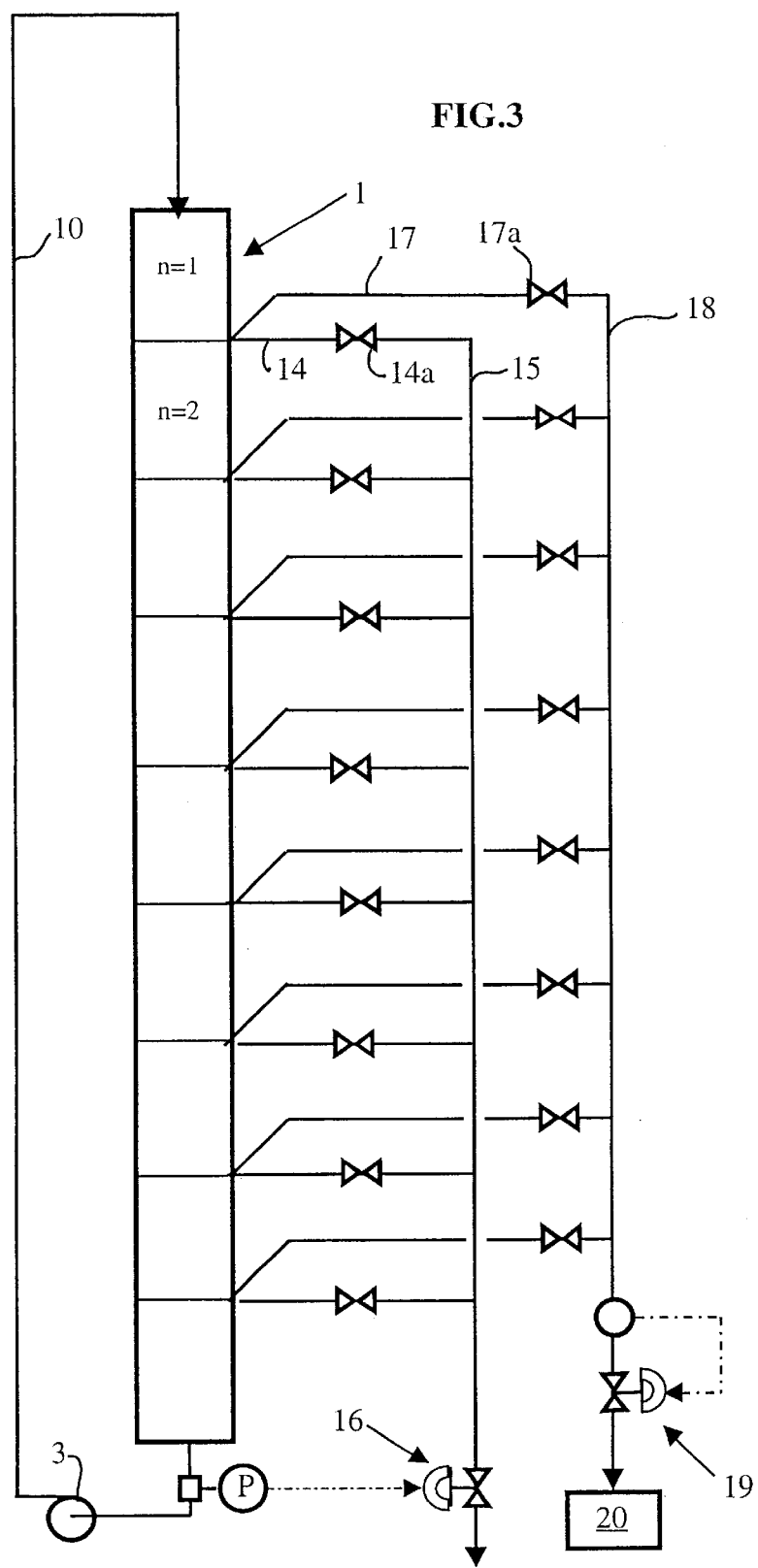
FIG. 3 illustrates the continuous production of the first raffinate and the intermittent production of the second raffinate according to the invention, for the duration of a fraction of a period.

FIG. 3 illustrates the continuous production of first raffinate R1 and the intermittent production of second raffinate R2, whereby the second raffinate flows only during a fraction of the period.

The elements of the device that are referenced in FIG. 3 are the same as those of FIG. 1.

Line 15 that collects first raffinate R1 is under pressure monitoring, whereby R1 is produced continuously while line 16 that recovers second raffinate R2 is under flow monitoring. Between each two beds are connected a line that is dedicated to R1 and a line that is dedicated to R2.

The device according to FIG. 3 can operate in the following manner:

During a portion of a period, a half-period for example, a minor portion of the raffinate is sampled in the form of the first raffinate between the first bed and the second bed via lines 14 and 15, and the remaining major part is sampled simultaneously in the form of the second raffinate, between the same two beds, via lines 17 and 18. During the remaining portion of the period, between the same two beds, the first raffinate is sampled completely (sum of the flow rates of R1 and R2) in lines 14 and 15 while the flow of the second raffinate is zero, whereby stop valve 17a on line 17 of the second raffinate is closed. The same operation is then repeated on the next bed during the next period.

Control means for opening and closing valves on the lines of raffinates that are not shown in the figures make it possible to implement the process according to continuous or intermittent draw-off operations of these raffinates R1 and R2.

They are generally associated with simultaneous periodic offsetting means of the injection positions of the feedstock and desorbent in the chromatographic column and the draw-off position of the extract of said column of a bed in the direction of flow of the main flux that circulates in the column.

EXAMPLE 1

The separation of a feedstock that comprises a mixture of xylenes and ethylbenzene of the following composition by weight:

| | | |
|---|---|---|
| PX: | paraxylene | 25% |
| MX: | metaxylene | 44.2% |
| OX: | orthoxylene | 20.8% |
| EB: | ethylbenzene | 10.0% | is carried out in a simulated moving bed in countercurrent in two cylindrical adsorbers that measure 1 m² in section and that consist of 24 beds that contain a barium-exchanged X zeolite.

The optimized operating conditions (flow rate) are as follows:

| | |
|---|---|
| Feedstock: | 9.5 m³/h |
| Solvent: | 16.15 m³/h of paradiethylbenzene |
| Extract: | 9.1 m³/h |
| Raffinate: | 16.54 m³/h |
| Recycling flow rate (in zone 1): | 52.2465 m³/h |

Recycling flow rate (in zone 1): 52.2465 m³/h

The switching time of the valves (or period) is 80 seconds.

After distillation of the paradiethylbenzene, the extract that is obtained delivers paraxylenes with 99.84% purity and a yield of 95.53%.

The 16.54 m³/h of single raffinate is distilled, and after separation of desorbent and then of orthoxylene, a flow rate of metaxylene-enriched fluid of 3.06 m³/h is obtained whose composition is as follows:

| | |
|---|---|
| PX: | 1.76% |
| MX: | 82.87% |
| OX: | 0.1% |
| Ethylbenzene: | 15.87% |

The MX purity is 82.87%.

EXAMPLE 2

The feedstock of Example 1 that is introduced into the two adsorbers of Example 1 operating in a simulated moving bed in countercurrent is used again. The flow rate operating conditions are those of Example 1.

The respective positions of injections and draw-offs are specified in Table 3 below.

The number of the bed is that of the bed that is located after the injection valve or draw-off valve. Thus, during the first period, the feedstock will be injected, for example, into bed 15, and first raffinate R1 will be drawn off before bed 20, whereby the draw-off valve of second raffinate R2 before bed 22 (between beds 21 and 22) is closed, hence the designation 22*0.

TABLE 3

Position of the Beds

| Period | Extract | Feedstock | Raf 1 | Raf 2 |
|---|---|---|---|---|
| 1 T | 6 | 15 | 20 | 22*0 |
| 2 T | 7 | 16 | 21*0 | 23 |
| 3 T | 8 | 17 | 22 | 24*0 |
| 4 T | 9 | 18 | 23*0 | 1 |
| 5 T | 10 | 19 | 24 | 2*0 |
| 6 T | 11 | 20 | 1*0 | 3 |
| 7 T | 12 | 21 | 2 | 4*0 |

According to this configuration, the proportion of R1 (impure raffinate) is 50%, and the proportion of pure raffinate (R2) is 50%. After distillation of the desorbent, then the orthoxylene, the composition of the collected product is:

| | |
|---|---|
| PX: | 0.11% |
| MX: | 98.96% |
| OX: | 0.12% |
| EB: | 0.80% | or a purity of MX of 98.96% for a yield of MX of 19.35%.

The splitting of the raffinate does not degrade the performance of the unit as far as purification of paraxylene is concerned since its purity reaches 99.79% for a yield of 95.7%.

EXAMPLE 3

Example 2 is repeated, but the opening and closing sequences of the valves of raffinates are as follows (Table 4):

TABLE 4

| Period | Desorbent | Extract | Feedstock | Raf 1 | Raf 2 |
|---|---|---|---|---|---|
| 1 T | 1 | 6 | 15 | 20 | 22*0 |
| 2 T | 2 | 7 | 16 | 21 | 23*0 |
| 3 T | 3 | 8 | 17 | 22*0 | 24 |
| 4 T | 4 | 9 | 18 | 23 | 1*0 |
| 5 T | 5 | 10 | 19 | 24 | 2*0 |
| 6 T | 6 | 11 | 20 | 1*0 | 3 |
| 7 T | 7 | 12 | 21 | 2 | 4*0 |

Raffinate 2 represents only 33% of the total raffinate (raffinate 1+raffinate 2).

After distillation from raffinate 2, its composition is as follows:

| | |
|---|---|
| PX: | 0.16% |
| MX: | 99.70% |
| OX: | 0.12% |
| EB: | 0.1% | or a purity of MX of 99.70%, better than that of MX of Example 2, but a reduced yield of 9.21%.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 00/05.424, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for co-production of metaxylene and paraxylene from a hydrocarbon feedstock wherein the process comprises a separation stage of the feedstock in a simulated moving bed in at least one chromatographic column containing a plurality of beds of an adsorbent, interconnected in a loop, said column comprising an injection of the feedstock, which contains at least 6% by weight of ethylbenzene, a draw-off of a first raffinate, a draw-off of a second raffinate comprising metaxylene, an injection of desorbent and a draw-off of an extract comprising paraxylene, whereby the process comprising simultaneous periodic offsetting of injection positions and draw-off position of the extract of a bed in the direction of flow of the main flux that circulates in the column, wherein a first raffinate comprising desorbent, orthoxylene, metaxylene and ethylbenzene is drawn off continuously or intermittently, said second raffinate comprising orthoxylene and metaxylene is drawn off intermittently, and the second raffinate is distilled to recover orthoxylene and metaxylene separately with at least 99% purity, and with yield of metaxylene of more than 10%.

2. A process according to claim 1, wherein during said simultaneous periodic offsetting injection positions and the draw-off position of the extract, the draw-off position of the first raffinate from one bed or two beds are moved forward in the direction of flow of the main flux.

3. A process according to claim 1, wherein during simultaneous periodic offsetting injection positions and the draw-off position of the extract, the draw-off position of the second raffinate from at least two beds or at most a submultiple of the total number of beds are moved forward, and the second raffinate is drawn off dining one period.

4. A process according to claim 1, wherein to draw off the first raffinate continuously, the first raffinate is drawn off from a bed during at least one period, and under pressure monitoring and during another period, a minor portion of the first raffinate is drawn off from another bed at a minimum flow rate that is compatible with a pressure monitoring, and a major portion of the second raffinate is drawn off simultaneously under flow monitoring.

5. A process according to claim 1, wherein the first raffinate is drawn off intermittently during one period, the pressure of the chromatographic column is controlled at the level of the feedstock, or desorbent or extract, and the first raffinate and the second raffinate are drawn off under flow monitoring.

6. A process according to claim 1, wherein from a bed n, the first raffinate is drawn off during a period Tn; simultaneously from bed n+2, a minor portion of the first raffinate and a major portion of the second raffinate are drawn off during next period Tn+1; the first raffinate is drawn off during next period Tn+2 from same bed n+2; from bed n+4, a minor portion of the first raffinate and a major portion of the second raffinate are drawn off during next period Tn+3, and so on.

7. A process according to claim 1, wherein during a period Tn and from a given bed n, the second raffinate and then the first raffinate are drawn off during next period Tn+1; from same bed n, no raffinate is drawn off from next bed n+1; the second raffinate is drawn off from next bed n+2 during period Tn+2, then the first raffinate during next period Tn+3 from same bed n+2, and so on.

8. A process according to claim 1, wherein the following sequence is carried out multiple times: in a given bed n, the second raffinate is drawn off during a period Tn; in same bed n, the first raffinate is drawn off during next period Tn+1; in next bed n+1, the first raffinate is drawn off during next period Tn+2, and no raffinate is drawn off in next bed n+2.

9. A process according to claim 1, wherein the following sequence is carried out multiple times: in a given bed n, the first raffinate is drawn off during a period Tn; in next bed n+1, the first raffinate is drawn off during a period Tn+1; in next bed n+2, the first raffinate is drawn off during a period Tn+2; no raffinate is drawn off in next bed n+3 for next period Tn+3, and a second raffinate is drawn off in next bed n+4 during same period Tn+3.

10. A process according to claim 1, wherein during simultaneous periodic offsetting of the injection positions and the draw-off position of the extract, the draw-off position of the second raffinate is moved forward by at least one bed or at most a submultiple of the total number of beds, and the second raffinate is drawn off during a fraction of the period.

11. A process according to claim 1, wherein during a fraction of the period, a minor portion of the first raffinate is drawn off under pressure monitoring, and a major portion of the second raffinate is drawn off under flow monitoring, then during the remaining portion of the period, only the first raffinate is drawn off from the same bed under pressure monitoring, and the sequence above is repeated in the next bed in the next period and so on.

12. A process according to claim 1, wherein said purity is at least 99.5%.

13. A process according to claim 5, wherein the pressure of the chromatographic column is controlled at the level of the feedstock.

14. A process according to claim 1, wherein the yield of metaxylene is greater than 15%.

15. A process according to claim 1, wherein the yield of metaxylene is about 15–20%.

16. A process according to claim 1, wherein the feedstock contains 10% by weight of ethylbenzene.

17. A process according to claim 1, wherein the first raffinate is drawn off intermittently.

18. A process according to claim 1, wherein the first raffinate is drawn off continuously.

* * * * *

UNITED STATES PATENT AND TRADEMARK OFFICE
CERTIFICATE OF CORRECTION

PATENT NO. : 6,696,616 B2
DATED : February 24, 2004
INVENTOR(S) : Didier Pavone et al.

It is certified that error appears in the above-identified patent and that said Letters Patent is hereby corrected as shown below:

<u>Column 9,</u>
Line 37, "dining" should read -- during --

Signed and Sealed this

Seventh Day of September, 2004

JON W. DUDAS
*Director of the United States Patent and Trademark Office*